United States Patent
Wicks et al.

(10) Patent No.: US 8,889,890 B2
(45) Date of Patent: Nov. 18, 2014

(54) KETAL ESTERS OF OXOCARBOXYLIC ACIDS AND PROCESS OF MAKING

(75) Inventors: Douglas A. Wicks, Plymouth, MN (US);
Sergey Selifonov, Plymouth, MN (US);
Marc Davis Scholten, Saint Paul, MN (US)

(73) Assignee: Segetis, Inc., Golden Valley, MN (US)

( * ) Notice: Subject to any disclaimer, the term of this patent is extended or adjusted under 35 U.S.C. 154(b) by 149 days.

(21) Appl. No.: 13/395,317

(22) PCT Filed: Sep. 13, 2010
(Under 37 CFR 1.47)

(86) PCT No.: PCT/US2010/048644
§ 371 (c)(1),
(2), (4) Date: Aug. 22, 2012

(87) PCT Pub. No.: WO2011/032095
PCT Pub. Date: Mar. 17, 2011

(65) Prior Publication Data
US 2012/0323024 A1    Dec. 20, 2012

Related U.S. Application Data

(60) Provisional application No. 61/241,433, filed on Sep. 11, 2009.

(51) Int. Cl.
*C07D 317/24* (2006.01)
*C07D 317/14* (2006.01)

(52) U.S. Cl.
CPC ............... *C07D 317/14* (2013.01)
USPC ........................................................ 549/375

(58) Field of Classification Search
CPC .................................................... C07D 319/06
USPC ........................................................ 549/375
See application file for complete search history.

(56) References Cited

U.S. PATENT DOCUMENTS

| 4,710,505 A | 12/1987 | Robin et al. |
| 5,498,743 A | 3/1996 | Shih et al. |
| 5,696,248 A | 12/1997 | Peyman et al. |

FOREIGN PATENT DOCUMENTS

| EP | 0688784 A2 | 12/1995 |
| WO | WO2006/033730 A2 | 3/2006 |

OTHER PUBLICATIONS

International Preliminary Report on Patentability for PCT/US2010/048644 mailed Mar. 22, 2012, 4 pages.
Transmittal of International Preliminary Report on Patentability for PCT/US2010/048644 mailed Mar. 22, 2012, 1 page.
International Search Report for PCT/US2010/048644, mailed Nov. 16, 2010, 6 pages.
Written Opinion for PCT/US2010/048644 mailed Nov. 16, 2010, 4 pages.

*Primary Examiner* — Taofiq A Solola
(74) *Attorney, Agent, or Firm* — Cantor Colburn LLP

(57) ABSTRACT

A ketal ester of an oxocarboxylic acid and a process to make the same, where the ketal ester is of Structure (I): wherein a is 0 or an integer from 1 to 12; n is 0 or 1; $R_1$ is a linear alkyl, aryl, arylalkylene, or branched alkyl group with 1-18 carbon atoms; $R_2$ and $R_5$ can be hydrogen, $C_{1-6}$ straight chain or branched alkyl, phenyl, substituted phenyl, C1-6 alkyl substituted with up to four OH groups, C1-6 alkyl, or acetyl optionally substituted hydrocarbon radicals, or $R_2$ and $R_4$ together with the α-carbon form a cycloaliphatic or heterocyclic ring with 3-6 carbon atoms and 0-3 heteroatoms, provided that only one of $R_2$ and $R_5$ is hydrogen; $R_3$ is a linear alkyl or branched alkyl group with 1-18 carbon atoms; and $R_4$ is hydrogen, or an alkyl, aryl, aralkyl or branched alkyl group with 1-10 carbon atoms.

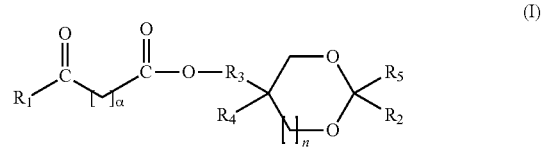

(I)

31 Claims, No Drawings

KETAL ESTERS OF OXOCARBOXYLIC ACIDS AND PROCESS OF MAKING

CROSS-REFERENCE TO RELATED APPLICATION

This application claims priority to U.S. Provisional Patent Application Ser. No. 61/241,433, filed Sep. 11, 2009, which is incorporated herein by reference in its entirety.

FIELD OF THE INVENTION

The invention relates generally to ketal compounds, and more specifically to ketal esters of oxocarboxylic acids and methods for their manufacture.

BACKGROUND

Many known chemical products such as surfactants, plasticizers, solvents, and polymers are currently manufactured from non-renewable, expensive, petroleum-derived or natural gas-derived feedstock compounds. High raw material costs and uncertainty of future supplies provide a need for the discovery and development of surfactants, plasticizers, solvents, polymers, and other chemical products that can be made from inexpensive renewable biomass-derived feedstocks and by simple chemical methods. Using renewable resources as feedstocks for chemical processes will reduce the demand on non-renewable fossil fuels currently used in the chemical industry and reduce the overall production of carbon dioxide, the most notable greenhouse gas.

It is desirable to provide commonly used chemical products, such as surfactants, plasticizers, solvents, polymers, and the like from renewable feedstocks as a source of chemical building blocks. There is further a need for chemical building blocks that are at least one of chemically and thermally stable. It would be a still further advantage for the chemical building blocks to have multiple functionalities for subsequent reactions. Moreover, it is desirable to provide such materials by simple and/or and reproducible methods.

SUMMARY

Ketal compounds can be prepared from a trihydric alcohol and an oxocarboxylic acid or derivative thereof. The ketal compounds are esters of an oxocarboxylic acid having Structure I:

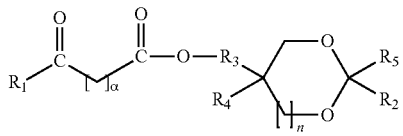

wherein
α is 0 or an integer from 1 to 12;
n is 0 or 1;
$R_1$ is a linear alkyl, aryl, arylalkylene, or branched alkyl group with 1-18 carbon atoms;
$R_2$ and $R_5$ can be the same or different and are hydrogen, $C_{1-6}$ straight chain or branched alkyl, phenyl, substituted phenyl, $C_{1-6}$ alkyl substituted with up to four $OR^8$ groups, wherein $R^8$ is hydrogen, $C_{1-6}$ alkyl, or acetyl optionally substituted hydrocarbon radicals, or $R_2$ and $R_4$ together with the α-carbon form a cycloaliphatic or heterocyclic ring with 3-6 carbon atoms and 0-3 heteroatoms, provided that only one of $R_2$ and $R_5$ is hydrogen;
$R_3$ is a linear alkyl or branched alkyl group with 1-18 carbon atoms; and
$R_4$ is hydrogen, alkyl, aryl, and arylalkylene or branched alkyl group with 1-10 carbon atoms.

In another embodiment, a process for making a ketal ester of an oxocarboxylic acid comprises reacting a hydroxy functional ketal of Structure II

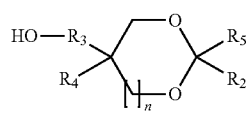

with an oxocarboxlic acid or reactive derivative thereof of Structure III:

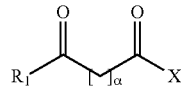

to form the ketal ester of an oxocarboxylic acid of Structure I, wherein each of $R_1$, $R_2$, $R_3$, $R_4$, $R_5$, and n are as previously defined, and X is a leaving group.

The details of one or more embodiments of the invention are set forth in the description below. Other features, objects, and advantages will be apparent from the description and from the claims.

DETAILED DESCRIPTION

Ketal esters of oxocarboxylic acids of Structure I and a method of making such ketal esters of oxocarboxylic acids are disclosed. The ketal esters of oxocarboxylic acids can be made utilizing one or more materials available from biorenewable sources. The process is simple, efficient, and reproducible. Such ketal esters are useful, for example as functional chemicals, or as intermediates in the production of polymers or functional chemicals.

Structure I is as follows:

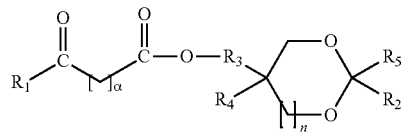

wherein
α is 0 or an integer from 1 to 12;
n is 0 or 1;
$R_1$ is a linear alkyl, aryl, arylalkylene, or branched alkyl group with 1-18 carbon atoms;
$R_2$ and $R_5$ can be the same or different and are hydrogen, $C_{1-6}$ straight chain or branched alkyl, phenyl, substituted phenyl, $C_{1-6}$ alkyl substituted with up to four $OR^8$ groups, wherein $R^8$ is hydrogen, $C_{1-6}$ alkyl, or acetyl optionally substituted hydrocarbon radicals, or $R_2$ and $R_4$ together with the α-carbon form a cycloaliphatic or heterocyclic ring with 3-6 carbon atoms and 0-3 heteroatoms, provided that only one of $R_2$ and $R_5$ is hydrogen;

$R_3$ is a linear alkylene or branched alkylene group with 1-18 carbon atoms;

$R_4$ is hydrogen, or an alkyl, aryl, arylalkylene or branched alkyl group with 1-10 carbon atoms.

In another aspect, $R_1$ is $C_{1-6}$ straight chain or branched alkyl or phenyl, $R_2$ is hydrogen, isobutyl, or methyl, $R_3$ is a $C_{1-12}$ straight chain alkyl, $R_4$ is hydrogen, methyl or ethyl, $R_5$ is hydrogen or methyl, n is 0, and α is an integer from 1-8.

In another aspect, $R_1$ is $C_{1-4}$ straight chain alkyl or phenyl, $R_2$ is hydrogen, isobutyl, or methyl, $R_3$ is a $C_{1-3}$ straight chain alkylene, $R_4$ is hydrogen, methyl or ethyl, $R_5$ is hydrogen or methyl, n is 0, and α is an integer from 1-8.

In another aspect, $R_1$ is methyl, ethyl or butyl, $R_2$ is hydrogen, isobutyl, or methyl, $R_3$ is a $C_{1-12}$ straight chain alkyl, $R_4$ is hydrogen, methyl or ethyl, $R_5$ is hydrogen or methyl, n is 0, and α is 1 or 2.

In still another aspect, $R_1$ is methyl, $R_2$ is methyl, $R_3$ is —$CH_2$—, $R_4$ is hydrogen, $R_5$ is methyl, n is 0, and α is 2.

Further in another aspect, $R_1$ is methyl, $R_2$ is methyl, $R_3$ is —$CH_2$—, $R_4$ is hydrogen, $R_5$ is methyl, n is 0 and α is 2.

Further in another aspect, $R_1$ is methyl, $R_2$ is methyl, $R_3$ is —$CH_2$—, $R_4$ is ethyl, $R_5$ is methyl, n is 1 and α is 2.

Further in another aspect, $R_1$ is methyl, $R_2$ is methyl, $R_3$ is —$CH_2$—, $R_4$ is ethyl, $R_5$ is methyl, n is 1 and α is 1.

Further in another aspect, $R_1$ is methyl, $R_2$ is isobutyl, $R_3$ is —$CH_2$—, $R_4$ is hydrogen, $R_5$ is methyl, n is 0 and α is 2.

Further in another aspect, $R_1$ is methyl, $R_2$ is isobutyl, $R_3$ is —$CH_2$—, $R_4$ is hydrogen, $R_5$ is methyl, n is 0 and α is 1.

Further in another aspect, $R_1$ is methyl, $R_2$ is isobutyl, $R_3$ is —$CH_2$—, $R_4$ is ethyl, $R_5$ is methyl, n is 0 and α is 2.

Even further in another aspect, $R_1$ is methyl, $R_2$ is methyl, $R_3$ is —$CH_2$—, $R_4$ is hydrogen, $R_5$ is methyl, n is 0 and α is 1.

Still further in another aspect, $R_1$ is methyl, $R_2$ is methyl, $R_3$ is —$CH_2$—, $R_4$ is hydrogen, $R_5$ is methyl, n is 0 and α is 0.

Yet further in another aspect, $R_1$ is methyl, $R_2$ is methyl, $R_3$ is —$CH_2$—, $R_4$ is ethyl, $R_5$ is methyl, n is 1 and α is 2.

The ketal esters of oxocarboxylic acids in accordance with Structure I can be prepared by the reaction of a hydroxy-functional ketal of Structure II with an oxocarboxylic-acid or reactive derivative thereof of Structure III. Structure II is as follows:

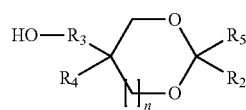

wherein $R_2$, $R_3$, $R_4$, $R_5$ and n are as described in Structure I.

In an aspect, $R_2$ is hydrogen, isobutyl, or methyl, $R_3$ is a $C_{1-12}$ straight chain alkylene, $R_4$ is hydrogen, methyl, or ethyl, $R_5$ is hydrogen or methyl, and n is 0 or 1.

In another aspect, $R_2$ is hydrogen, isobutyl, or methyl, $R_3$ is a $C_{1-3}$ straight chain alkyl, $R_4$ is hydrogen, methyl, or ethyl, $R_5$ is hydrogen or methyl, and n is 0.

Further in another aspect, $R_2$ is methyl, $R_3$ is —$CH_2$—, $R_4$ is ethyl, $R_5$ is methyl, n is 1 and α is 2 (covers TMP).

Further in another aspect, $R_2$ is methyl, $R_3$ is —$CH_2$—, $R_4$ is ethyl, $R_5$ is methyl, and n is 1.

Further in another aspect, $R_2$ is isobutyl, $R_3$ is —$CH_2$—, $R_4$ is hydrogen, $R_5$ is methyl, and n is 0.

Further in another aspect, $R_2$ is isobutyl, $R_3$ is —$CH_2$—, $R_4$ is ethyl, $R_5$ is methyl, and n is 0.

Further another aspect, $R_2$ is methyl, $R_3$ is —$CH_2$—, $R_4$ is hydrogen, $R_5$ is methyl, and n is 0. This compound is known in the art as "solketal."

Further in another aspect, $R_2$ is methyl, $R_3$ is —$CH_2$—, $R_4$ is ethyl, $R_5$ is methyl, and n is 1.

Suitable oxocarboxylic acids and reactive derivatives thereof that can be reacted with the functional ketal compounds of Structure II are of Structure III:

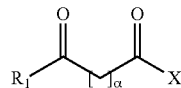

wherein α and $R_1$ are as defined in Structure I, and X is a leaving group, for example, a halide, —OH, —$OR_9$, or —O—(C=O)—$R_9$ wherein each $R_9$ is a $C_{1-6}$ hydrocarbon, for example as a $C_{1-6}$ straight chain or branched alkyl.

Examples of suitable oxocarboxylic acids and reactive derivatives thereof include, but are not limited to, 2-oxo-propionic acid and its halides, esters, and hydrocarbonyloxy derivatives, 3-oxo-butyric acid and its and its halides, esters, and hydrocarbonyloxy derivatives, 4-oxo-pentanoic acid and its and its halides, esters, and hydrocarbonyloxy derivatives, 5-oxo-hexanoic acid and its and its halides, esters, and hydrocarbonyloxy derivatives, 7-oxo-octanoic acid and its and its halides, esters, and hydrocarbonyloxy derivatives, 6-oxo-heptanoic acid and its and its halides, esters, and hydrocarbonyloxy derivatives, and 4-oxo-4-phenyl-butyric acid, and its and its halides, esters, and hydrocarbonyloxy derivatives.

In an embodiment, the esters or hydrocarbonyloxy derivatives are used. In another embodiment, the oxocarboxylic acid or derivative thereof of Structure III is 2-oxo-propionic acid, a $C_{1-3}$ alkyl ester of 2-oxo-propionic acid, 3-oxo-butyric acid, a $C_{1-3}$ alkyl ester of 3-oxo-butyric acid , 4-oxo-pentanoic acid, a $C_{1-3}$ alkyl ester of 4-oxo-pentanoic acid, 5-oxo-hexanoic acid, a $C_{1-3}$ alkyl ester of 5-oxo-hexanoic acid, 7-oxo-octanoic acid, a $C_{1-3}$ alkyl ester of 7-oxo-octanoic acid, 6-oxo-heptanoic acid, a $C_{1-3}$ alkyl ester of 6-oxo-heptanoic acid, 4-oxo-4-phenyl-butyric acid, a $C_{1-3}$ alkyl ester of 4-oxo-4-phenyl-butyric acid, or a combination thereof.

The reaction of the hydroxyl-functional ketals of Structure II with the oxocarboxylic acid or reactive derivative thereof of Structure III in the present application can be conducted under conditions effective for reaction of an alcohol with a carboxylic acid, acid chloride, acid, or hydrocarbonyloxy derivative, provided that such conditions do not unduly lead to undesired side reactions, such as loss of the ketal group in the hydroxyl-functional ketals of Structure II or the product of Structure III. Thus, acid conditions are generally avoided, unless particular care is taken to prevent loss of the ketal functionality. General conditions for the reaction of the hydroxyl-functional ketals of Structure II with the oxocarboxylic acid or reactive derivative thereof of Structure III are known in the art, and can be determined without undue experimentation.

In an embodiment, the reaction is a transesterification of the ester derivative of Structure III wherein X is $OR_9$ and the alcohol of Structure II in the presence of a catalyst.

For example, enzyme-mediated transesterifications can be used. The enzymes useful herein are typically those that catalyze transesterification of esters and/or esterification of carboxylic acids, and/or hydrolysis of esters. Typical types of enzymes that may be used include lipases, proteases, and esterases. Lipase enzymes are efficient transesterification catalysts that can be used in solution or immobilized. Immobilized enzymes can be more stable than free enzymes, and are readily removed from the reaction medium by simple filtration. Lipase enzymes can be immobilized onto various polymers support without significant loss in activity. Such transesterifications are aqueous, and generally free of any organic solvents. Transesterification can reach quantitative conversion with no or substantially no side products. Workup of the crude product is accomplished by filtration and removal of the immobilized enzymes, which can be washed and recycled.

The enzymatic processes herein are performed at temperatures at which the enzymes are active as catalysts for the desired reactions. The upper temperature limit is typically that at which the enzyme ceases to be an active catalyst. Oftentimes this is the temperature at which the enzyme is denatured in the reaction medium. This upper temperature will vary with the enzyme used and the process ingredients, especially the preselected solvent, used. Typically these temperatures may range from about 0° C. to about 130° C. (the latter using specialty enzymes for higher temperatures, such as enzymes isolated from thermophilic microorganisms). Higher temperatures (but below the temperature at which the enzyme ceases to be active) are usually preferred because reaction(s) are often faster and solubilities of the various process ingredients are usually higher at higher temperatures. In an embodiment transesterification proceeds at relatively low temperature (e.g., 25-60° C.), Examples of other types of catalysts include, but are not limited to, alkali metals or alkaline earth metals, such as lithium, sodium, potassium, rubidium, cesium, magnesium, calcium, strontium, barium and the like; basic compounds such as hydrides, hydroxides, alkoxides, aryloxides and amides of alkali metals or alkaline earth metals and the like; basic compounds, such as carbonates and hydrogencarbonates of alkali metals or alkaline earth metal, alkali metal or alkaline earth metal salts of organic acids and the like; tertiary amines such as triethylamine, tributylamine, trihexylamine, benzyldiethylamine and the like; nitrogen-containing heteroaromatic compounds, such as N-alkylpyrrole, N-alkylindole, oxazole, N-alkylimidazole, N-alkylpyrazole, oxadiazole, pyridine, alkylpyridine, quinoline, alkylquinoline, isoquinoline, alkylisoquinoline, acridine, alkylacridine, phenanthroline, alkylphenanthroline, pyrimidine, alkylpyrimidine, pyradine, alkylpyradine, triazine, alkyltriazine and the like; cyclic amidines, such as diazabicycloundecene (DBU), diazabicyclononene (DBN) and the like; thallium compounds, such as thallium oxide, thallium halides, thallium hydroxide, thallium carbonate, thallium nitrate, thallium sulfate, thallium salts of organic acids and the like; tin compounds, such as tributylmethoxytin, tributylethoxytin, dibutyldimethoxytin, diethyldiethoxytin, dibutyldiethoxytin, dibutylphenoxytin, diphenylmethoxytin, dibutyltin acetate, tributyltin chloride, tin 2-ethylhexanoate and the like; zinc compounds, such as dimethoxyzinc, diethoxyzinc, ethylenedioxyzinc, dibutoxyzinc and the like; aluminum compounds such as aluminum trimethoxide, aluminum triisopropoxide, aluminum tributoxide and the like; titanium compounds, such as tetramethoxytitanium, tetraethoxytitanium, tetrabutoxytitanium, dichlorodimethoxytitanium, tetraisopropoxytitanium, titanium acetate, titanium acetylacetonate and the like; phosphorus compounds, such as trimethylphosphine, triethylphosphine, tributylphosphine, triphenylphosphine, tributylmethylphosphonium halides, trioctylbutylphosphonium halides, triphenylmethylphosphonium halides and the like; zirconium compounds, such as zirconium halides, zirconocenes, zirconium acetylacetonate, zirconium alkoxides, zirconium acetate and the like; lead and lead-containing compounds, e.g., lead oxides, such as PbO, $PbO_2$, $Pb_3O_4$ and the like; lead sulfides, such as PbS, $Pb_2S_3$, $PbS_2$ and the like; lead hydroxides, such as $Pb(OH)_2$, $Pb_3O_2(OH)_2$, $Pb_2[PbO_2(OH)_2]$, $Pb_2O(OH)_2$ and the like; plumbites, such as $Na_2PbO_2$, $K_2PbO_2$, $NaHPbO_2$, $KHPbO_2$ and the like; plumbates, such as $Na_2PbO_3$, $Na_2H_2PbO_4$, $K_2PbO_3$, $K_2[Pb(OH)_6]$, $K_4PbO4$, $Ca_2PbO_4$, $CaPbO_3$ and the like; lead carbonates and basic salts thereof, such as $PbCO_3$, $PbCO_3.Pb(OH)_2$ and the like; alkoxylead compounds and aryloxylead compounds, such as $Pb(OCH_3)_2$, $(CH_3O)Pb(OPh)$, $Pb(OPh)_2$ and the like; lead salts of organic acids, and carbonates and basic salts thereof, such as $Pb(OCOCH_3)_2$, $Pb(OCOCH_3)_4$, $Pb(OCOCH_3)_2.PbO.3H_2O$, and the like; organolead compounds, such as $BU_4Pb$, $Ph_4Pb$, $Bu_3PbCl$, $Ph_3PbBr$, $Ph_3Pb$ (or $Ph_6Pb_2$), $Bu_3PbOH$, $Ph_2PbO$ and the like wherein Bu represents a butyl group and Ph represents a phenyl group; lead alloys, such as Pb—Na, Pb—Ca, Pb—Ba, Pb—Sn, Pb—Sb, and the like; lead minerals, such as galena, zinc blend and the like; hydrates of these lead compounds; ion-exchangers, such as anion-exchange resins having tertiary amino groups, amide groups, or at least one type of ion-exchange group selected from the group consisting of sulfonate, carboxylate and phosphate groups; strongly basic solid anion-exchangers having quaternary ammonium groups as ion-exchange groups and the like; solid inorganic compounds, such as silica, silica-alumina, silica-magnesia, aluminosilicate, gallium silicate, various types of zeolites, various types of metal-exchanged zeolites, ammonium-exchanged zeolites; and the like.

Specific heterogeneous transesterification catalysts include anion exchange resins having tertiary amine, quaternary ammonium, sulfonic acid or carboxylic acid functional groups, solid support catalysts containing alkaline earth metal halides, such as those described in U.S. Pat. No. 5,498,743, which is incorporated herein by reference, or inorganic solid support catalysts alone, such as alumina, pseudoboehmite, MgO and $MgO/Al_2O_3$ hydrotalcites, or containing ions, metals, compound or complexes of at least one element of Groups 1, 2, 4-10, 12 and 13-17 (IUPAC classification, previously Groups 1A, 2A, 4B-8B,2B and 3A-7A) of the Periodic Table.

Solvents and conditions (e.g., temperature, reaction time, and concentration and reactant amounts) for nonenzymatic catalysts are known in the art, and can be determined without undue experimentation. Solvent selection, for example, is guided by considerations such as catalyst selected, the particular reactants, cost, ease of removal, recyclability, and the like. Reaction temperature is selected based on considerations such as solvent selected, catalyst selected, the particular reactants, cost, stability of the reactants and products, and the like. Effective temperatures are generally 25-130° C., specifically 30-65° C. Reaction progress can be monitored by methods known in the art such as gas-chromatography-mass spectrometry (GC-MS).

To obtain the compounds of Structure II, trihydric alcohols of Structure IV can be reacted with a ketone of Structure V. Such trihydric alcohols are of Structure IV:

IV

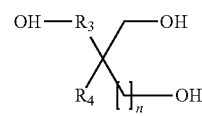

wherein n, $R_3$ and $R_4$ are as defined in Structure I. Ketones are of Structure V:

V wherein $R_2$ and $R_5$ are as defined in Structure I.

Non-limiting examples of trihydric alcohols include glycerol, trimethylol ethane, trimethylol propane, 1,2,4-trihydroxy butane, 1,2,5-trihydroxy pentane, 1,2,6-trishydroxy hexane, 1,2,7-trihydroxy heptane, 1,2,3-trihydroxy octane, 1,2,3-trihydroxy nonan, 1,2,4-trihydroxy nonan, 1,2,3-trihydroxy undecane, 1,2,3-trihydroxy dodecane, 1,2,11-trihydroxyundecane, 1,2,12-trihydroxydodecane, and combinations thereof.

Non-limiting examples of ketones include 2-propanone, 2-butanone, methylamyl ketone, methyl isobutyl ketone, acetophenone, benzophenone, and cyclohexanone.

Methods for the synthesis and isolation of hydroxy-functional ketals of Structure II are known in the art.

The compounds and methods described herein have a number of advantages. One or more of the starting materials (e.g., the oxocarboylic ester or derivative thereof and/or the trihydric alcohol can be derived from renewable feedstocks. The products of Structure I can be chemically and thermally stable. The products of Structure I further have multiple functionalities for subsequent reactions. Moreover, methods for the production of reactants II and III, as well as product I, can be simple and/or and reproducible.

The following is an example of the process, which is not intended to be limiting.

EXAMPLE

Discussed below is an enzymatic procedure for transesterification of oxcarboxylic esters, in particular levulinic esters with various alcohols. The procedure is organic solvent-free, proceeds at relatively low temperature (25-60° C.), and reaches quantitative conversion within 16 hours with no or substantially no side products observed. Workup of the crude product is accomplished by filtration, and the immobilized enzyme can be washed and recycled.

In this example, an excess of ethyl levulinate is transesterified with solketal in the presence of an immobilized lipase catalyst, generating solketal levulinate. Ethanol is liberated in the transesterification and removed under vacuum. A reaction scheme for the enzymatic transesterification of ethyl levulinate with solketal to make solketal levulinate is illustrated immediately below.

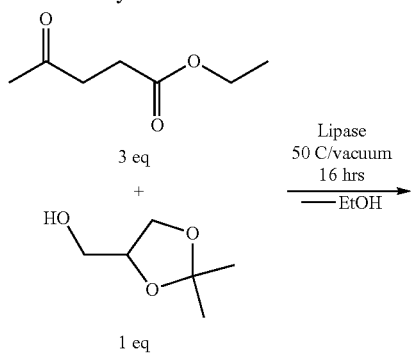

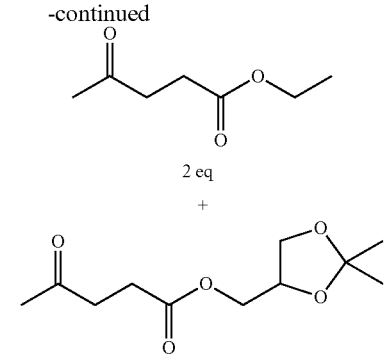

Molecular Weight: 230.26

Thus, to an empty three-neck round-bottom flask equipped with a magnetic stir bar and internal temperature probe was added ethyl levulinate (Aceto, 49.7 g, 0.34 mol) and solketal (Acros, 15.5 g, 0.12 mol). The reactor was equipped with a Dean-Stark trap and heated to 50° C. with stirring at 500 rpm under 3 ton vacuum for 2 hours. At this point, the water content of the reaction mixture was determined to be 356 ppm by Karl-Fisher titration. The reaction mixture was sampled for GC-FID analysis, and then catalyst was added (Lipase B from *candido antarctica*, Sigma, 1.49 g). After heating at 60° C. with stirring at 500 rpm under 6 torr vacuum for two hours, the reaction mixture was analyzed by the GC-FID and determined to have the composition shown in Table 1.

TABLE 1

| Retention Time (min.) | Area % | I.D. |
|---|---|---|
| 7.49 | 10.1 | solketal |
| 8.84 | 69.4 | Ethyl levulinate |
| 12.37 | 19.0 | Solketal levulinate |

After this sampling, the reaction mixture was heated at 60° C. with stirring at 500 rpm under 7 torr vacuum for an additional 66 hours. At this point the reaction mixture was sampled again and analyzed by the GC-FID. The composition of the reaction mixture is shown in Table 2.

TABLE 2

| Retention Time (min.) | Area % | I.D. |
|---|---|---|
| 7.47 | 0.2 | solketal |
| 8.84 | 57.0 | Ethyl levulinate |
| 12.38 | 39.5 | Solketal levulinate |

The structure of solketal levulinate was confirmed by GC-MS: retention time=11.2 minutes, m/z=215 (M-CH$_3$). In a separate run of the reaction, a similar level of solketal conversion was accomplished after 16 hrs.

As used herein, the singular forms "a," "an" and "the" are intended to include the plural forms as well, unless the context clearly indicates otherwise. The endpoints of all ranges directed to the same component or property are inclusive of the endpoint and independently combinable.

Unless otherwise defined, all terms (including technical and scientific terms) used herein have the same meaning as commonly understood by one of ordinary skill in the art to which this invention belongs.

Compounds are described using standard nomenclature. Any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein "alkyl" refers to a saturated aliphatic hydrocarbon having the specified number of carbon atoms, specifically 1 to 12 carbon atoms, more specifically 1 to 6 carbon atoms. "Alkylene" refers to a straight or branched divalent aliphatic hydrocarbon group, and may have from 1 to 12 carbon atoms, more specifically 1 to about 6 carbon atoms. "Aryl" means a cyclic moiety in which all ring members are carbon and at least one ring is aromatic. More than one ring may be present, and any additional rings may be independently aromatic, saturated or partially unsaturated, and may be fused, pendant, spirocyclic or a combination thereof. "Arylene" refers to a divalent radical formed by the removal of two hydrogen atoms from one or more rings of an aromatic hydrocarbon, wherein the hydrogen atoms may be removed from the same or different rings (preferably different rings), each of which rings may be aromatic or nonaromatic. The group —O—(C=O)—$R_9$ is referred to as a "hydrocarbonyloxy" group. "Arylalkylene" means a group having an aryl group covalently bonded to an alkylene group bonded to both the aryl group and the position being substituted, "Halide" means fluorine, chlorine, bromine, or iodine, "Heteroatoms" are independently selected from N, O, S, P, and Si. A combination of heteroatoms can be present.

As used herein, the term "substituted" refers to a compound or radical substituted with at least one (e.g., 1, 2, 3, or 4) substituents independently selected from a halide, a hydroxyl, a $C_{1-6}$ linear or branched alkyl, a $C_{1-6}$ cycloalkyl, a $C_{1-6}$ fluoroalkyl, a $C_{1-6}$ perfluoroalkyl($C_nF_{2n+1}$), a $C_{1-6}$ linear or branched alkoxy, a $C_{3-6}$ cylcoalkoxy, a $C_{3-6}$ linear or branched alkoxyalkyl, a nitro, a cyano, an amino, a carbonyl, a thiol, a $C_{1-6}$ alkoxylcarbonyl, a carboxyl, or a combination thereof, instead of hydrogen, provided that the substituted atom's normal valence is not exceeded. In a specific embodiment, a group is optionally substituted with a halide, a hydroxyl, a $C_{1-6}$ linear or branched alkyl, a $C_{1-6}$ fluoroalkyl, a $C_{1-6}$ perfluoroalkyl($C_nF_{2n+1}$), a $C_{1-6}$ linear or branched alkoxy, a nitro, a cyano, or a combination thereof.

For convenience, "ketal" is inclusive of acetals, e.g., compounds of Structures I and II wherein one of $R_2$ or $R_5$ is hydrogen.

The respective compounds disclosed herein can have one or more isomers. Where an isomer of the compound can exist, it should be understood that the disclosure herein embodies all isomers thereof, including stereoisomers, conformational isomers, and cis, trans isomers; isolated isomers thereof; and mixtures thereof.

All cited patents, patent applications, and other references are incorporated herein by reference in their entirety.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A ketal ester of an oxocarboxylic acid, the ketal ester having Structure I:

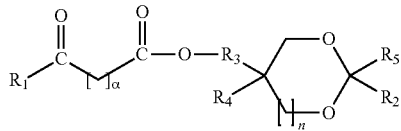

wherein
$\alpha$ is 0 or an integer from 1 to 12;
n is 0 or 1;
$R_1$ is a linear alkyl, aryl, arylalkylene, or branched alkyl group with 1-18 carbon atoms;
$R_2$ is isobutyl;
$R_5$ is hydrogen, $C_{1-6}$ straight chain or branched alkyl, phenyl, substituted phenyl, $C_{1-6}$ alkyl substituted with up to four $OR^8$ groups, wherein $R^8$ is hydrogen or a $C_{1-6}$ alkyl,
$R_3$ is a linear alkyl or branched alkyl group with 1-18 carbon atoms; and
$R_4$ is hydrogen, alkyl, aryl, and arylalkylene or branched alkyl group with 1-10 carbon atoms.

2. The ketal ester of claim 1, wherein $R_1$ is a $C_{1-6}$ straight chain or branched alkyl or phenyl, $R_3$ is a $C_{1-12}$ straight chain alkyl, $R_4$ is hydrogen, methyl or ethyl, $R_5$ is hydrogen or methyl, n is 0, and $\alpha$ is an integer from 1-8.

3. The ketal ester of claim 1, wherein $R_1$ is a $C_{1-4}$ straight chain alkyl, $R_3$ is a $C_{1-3}$ straight chain alkyl, $R_4$ is hydrogen, methyl or ethyl, $R_5$ is hydrogen or methyl, n is 0, and $\alpha$ is an integer from 1-8.

4. The ketal ester of claim 1, wherein $R_1$ is methyl, ethyl or butyl, $R_3$ is a $C_{1-12}$ straight chain alkyl, $R_4$ is hydrogen, methyl or ethyl, $R_5$ is hydrogen or methyl, n is 0, and $\alpha$ is 1 or 2.

5. The ketal ester of claim 1, wherein $R_1$ and $R_5$ are methyl, $R_3$ is —$CH_2$—, $R_4$ is hydrogen, n is 0 and $\alpha$ is 2.

6. The ketal ester of claim 1, wherein $R_1$ and $R_5$ are methyl, $R_3$ is —$CH_2$—, $R_4$ is hydrogen, n is 0 and $\alpha$ is 1.

7. The ketal ester of claim 1, wherein $R_1$ and $R_5$ are methyl, $R_3$ is —$CH_2$—, $R_4$ is hydrogen, n is 0 and $\alpha$ is 0.

8. The ketal ester of claim 1, wherein $R_1$ and $R_5$ are methyl, $R_3$ is —$CH_2$—, $R_4$ is ethyl, n is 1 and $\alpha$ is 2.

9. The ketal ester claim 1, wherein $R_1$ and $R_5$ are methyl, $R_3$ is —$CH_2$—, $R_4$ is hydrogen, $R_5$ is methyl, n is 0, and $\alpha$ is 2.

10. The ketal ester of claim 1, wherein $R_1$ is methyl, $R_3$ is —$CH_2$—, $R_4$ is hydrogen, $R_5$ is methyl, n is 0 and $\alpha$ is 2.

11. The ketal ester of claim 1, wherein $R_1$ is methyl, $R_3$ is —$CH_2$—, $R_4$ is ethyl, $R_5$ is methyl, n is 1 and $\alpha$ is 2.

12. The ketal ester of claim 1, wherein $R_1$ is methyl, $R_3$ is —$CH_2$—, $R_4$ is ethyl, $R_5$ is methyl, n is 1 and $\alpha$ is 1.

13. The ketal ester of claim 1, wherein $R_1$ is methyl, $R_3$ is —$CH_2$—, $R_4$ is ethyl, $R_5$ is methyl, n is 0 and $\alpha$ is 2.

14. A process for making a ketal ester of oxocarboxylic acid of Structure I,

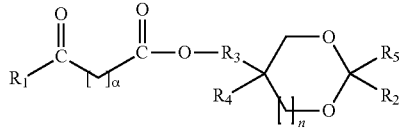

wherein
$\alpha$ is 0 or an integer from 1 to 12;
n is 0 or 1;

$R_1$ is a linear alkyl, aryl, arylalkylene, or branched alkyl group with 1-18 carbon atoms;

$R_2$ is isobutyl $R_5$ is hydrogen, $C_{1-6}$ straight chain or branched alkyl, phenyl, substituted phenyl, $C_{1-6}$ alkyl substituted with up to four $OR^8$ groups, wherein $R^8$ is hydrogen or a $C_{1-6}$ alkyl;

$R_3$ is a linear alkyl or branched alkyl group with 1-18 carbon atoms; and $R_4$ is hydrogen, or an alkyl, aryl, aralkyl or branched alkyl group with 1-10 carbon atoms, the method comprising:

reacting a hydroxy functional ketal of Structure II:

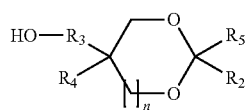

II wherein $R_2$, $R_3$, $R_4$, $R_5$, and n are as in Structure I, with an oxocarboxylic acid Structure III:

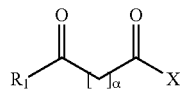

III wherein $\alpha$ and $R_1$ are as defined in Structure I and X is a halide, hydroxyl, —$OR_9$ or —O—(C=O)—$R_9$, wherein $R_9$ is a $C_{1-6}$ straight chain or branched alkyl, to form the ketal ester of oxocarboxylic acid of Structure I.

15. The process of claim 14, wherein the oxocarboxylic acid or derivative thereof of Structure III is 2-oxo-propionic acid, a $C_{1-3}$ alkyl ester of 2-oxo-propionic acid, 3-oxo-butyric acid, a $C_{1-3}$ alkyl ester of 3-oxo-butyric acid, 4-oxo-pentanoic acid, a $C_{1-3}$ alkyl ester of 4-oxo-pentanoic acid, 5-oxo-hexanoic acid, a $C_{1-3}$ alkyl ester of 5-oxo-hexanoic acid, 7-oxo-octanoic acid, a $C_{1-3}$ alkyl ester of 7-oxo-octanoic acid, 6-oxo-heptanoic acid, a $C_{1-3}$ alkyl ester of 6-oxo-heptanoic acid, 4-oxo-4-phenyl-butyric acid, a $C_{1-3}$ alkyl ester of 4-oxo-4-phenyl-butyric acid, or a combination thereof.

16. The process of claim 14, wherein the hydroxyl functional ketal of Structure II is formed by reacting a trihydric alcohol of Structure IV:

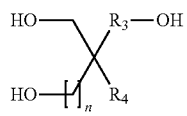

IV wherein n, $R_3$ and $R_4$ are as in Structure I, with a ketone of Structure V:

V wherein $R_2$ and $R_5$ are as defined in Structure I.

17. The process of claim 14, wherein the hydroxyl functional ketal of Structure II is formed by reacting trihydric alcohol selected from glycerol, trimethylol ethane, trimethylol propane, 1,2,4-trihydroxy butane, 1,2,5-trihydroxy pentane, 1,2,6-trishydoxy hexane, 1,2,7-trihydroxy heptane, 1,2,3-trihydroxy octane, 1,2,3-trihydroxy nonane, 1,2,4-trihydroxy nonane, 1,2,3 trihydroxy undecane, 1,2,3-trihydroxy dodecane, 1,2,11-trihydroxyundecane, 1,2,12-trihydroxydodecane or a mixture thereof with a ketone selected from 2-propanone, 2-butanone, methylamyl ketone, methyl isobutyl ketone, acetophenone, benzophenone, cyclohexanone, or a combination thereof.

18. The process of claim 14, wherein $R_1$ is a $C_{1-6}$ straight chain or branched alkyl or phenyl, $R_3$ is a $C_{1-12}$ straight chain alkyl, $R_4$ is hydrogen, methyl or ethyl, $R_5$ is hydrogen or methyl, n is 0, and $\alpha$ is an integer from 1-8.

19. The process of claim 14, wherein $R_1$ is a $C_{1-4}$ straight chain alkyl, $R_3$ is a $C_{1-3}$ straight chain alkyl, $R_4$ is hydrogen, methyl or ethyl, $R_5$ is hydrogen or methyl, n is 0, and $\alpha$ is an integer from 1-8.

20. The process of claim 14, wherein $R_1$ is methyl, ethyl or butyl, $R_3$ is a $C_{1-12}$ straight chain alkyl, $R_4$ is hydrogen, methyl or ethyl, $R_5$ is hydrogen or methyl, n is 0, and $\alpha$ is 1 or 2.

21. The process of claim 14, wherein $R_1$ and $R_5$ are methyl, $R_3$ is —$CH_2$—, $R_4$ is hydrogen, n is 0 and $\alpha$ is 2.

22. The process of claim 14, wherein $R_1$ and $R_5$ are methyl, $R_3$ is —$CH_2$—, $R_4$ is hydrogen, n is 0 and $\alpha$ is 1.

23. The process of claim 14, wherein $R_1$ and $R_5$ are methyl, $R_3$ is —$CH_2$—, $R_4$ is hydrogen, n is 0 and $\alpha$ is 0.

24. The process of claim 14, wherein $R_1$ and $R_5$ are methyl, $R_3$ is —$CH_2$—, $R_4$ is ethyl, n is 1 and $\alpha$ is 2.

25. The process of claim 14, wherein $R_1$ and $R_5$ are methyl, $R_3$ is —$CH_2$—, $R_4$ is hydrogen, $R_5$ is methyl, n is 0, and $\alpha$ is 2.

26. The process of claim 14, wherein $R_1$ is methyl, $R_3$ is —$CH_2$—, $R_4$ is ethyl, $R_5$ is methyl, n is 1 and $\alpha$ is 2.

27. The process of claim 14, wherein $R_1$ is methyl, $R_3$ is —$CH_2$—, $R_4$ is ethyl, $R_5$ is methyl, n is 1 and $\alpha$ is 1.

28. The process of claim 14, wherein $R_1$ is methyl, $R_3$ is —$CH_2$—, $R_4$ is ethyl, $R_5$ is methyl, n is 0 and $\alpha$ is 2.

29. The process of claim 14, wherein X is —$OR_9$ or —O—(C=O)—$R_9$, wherein $R_9$ is a $C_{1-6}$ straight chain or branched alkyl.

30. The process of claim 29, wherein the reaction is transesterifying in the presence of an enzyme catalyst selected from lipase, protease and esterase.

31. The process of claim 29, wherein enzyme catalyst is lipase.

* * * * *